United States Patent [19]
Sandberg et al.

[11] Patent Number: 5,920,388
[45] Date of Patent: Jul. 6, 1999

[54] SMALL PARTICLE CHARACTERISTIC DETERMINATION

[75] Inventors: Jon C. Sandberg, Boulder; Nelson C. Turner, Longmont; Richard C. Gallant, Boulder, all of Colo.

[73] Assignee: Research Electro-Optics, Inc., Boulder, Colo.

[21] Appl. No.: 08/729,948

[22] Filed: Oct. 15, 1996

[51] Int. Cl.$^6$ .................................................. G01J 3/30
[52] U.S. Cl. ........................................................ 356/315
[58] Field of Search .................................. 356/335–339, 356/315; 250/575, 574

[56] References Cited

U.S. PATENT DOCUMENTS

| | | |
|---|---|---|
| Re. 34,729 | 9/1994 | Sipes, Jr. . |
| 3,644,743 | 2/1972 | Binek et al. .................. 356/315 X |
| 3,825,345 | 7/1974 | Lorenz ........................ 356/335 |
| 4,281,924 | 8/1981 | Auer et al. . |
| 4,411,525 | 10/1983 | Ogawa . |
| 4,496,839 | 1/1985 | Bernstein et al. . |
| 4,571,079 | 2/1986 | Knollenberg . |
| 4,594,715 | 6/1986 | Knollenberg . |
| 4,653,056 | 3/1987 | Baer et al. . |
| 4,723,257 | 2/1988 | Baer et al. . |
| 4,739,507 | 4/1988 | Byer et al. . |
| 4,764,013 | 8/1988 | Johnston . |
| 4,798,465 | 1/1989 | Knollenberg . |
| 4,809,291 | 2/1989 | Byer et al. . |
| 4,872,177 | 10/1989 | Baer et al. . |
| 5,075,552 | 12/1991 | McClelland et al. . |
| 5,156,461 | 10/1992 | Moslehi et al. . |
| 5,642,193 | 6/1997 | Girvin et al. ................. 356/339 |
| 5,654,797 | 8/1997 | Moreau et al. ............... 356/338 |

OTHER PUBLICATIONS

Aerosol–Particle Sizes from Light Emission During Excitation by TEA CO2 Laser Pulses: Weeks and Duley; Journal of Applied Physics, vol. 45, No. 10, Oct. 1974, pp. 4661, 4662.

Soot Diagnostics Based on Laser Heating: Melton; Applied Optics, vol. 23, No. 13, Jul. 1984, pp. 2201–2208.

Flourescence of Atmospheric Aerosols and Lidar Implications: Gelbwachs and Birnbaum; Applied Optics, vol. 12, No. 10, Oct. 1973; pp. 2442–2447.

Primary Examiner—K P Hantis
Attorney, Agent, or Firm—Robert E. Harris

[57] ABSTRACT

Small particle identification is disclosed. A high intensity light source provides light at a sensing region for contact with small particles at the sensing region to cause resulting light that includes scattered light and emitted light due to heating of optically absorbing particles to incandescence with the resulting light terminating if vaporization of the optically absorbing particles occurs. A laser, having a laser cavity with the sensing region within the laser cavity, preferably provides high intensity laser light in the laser cavity for contact with the small particles at the sensing region. Utilizing optical detection, predetermined particle characteristic determination is enabled, including particle size and composition of optically absorbing particles.

58 Claims, 7 Drawing Sheets

Fig_1

Fig_5

Fig_3D

Fig_3C

Fig_4

SMALL PARTICLE CHARACTERISTIC DETERMINATION

FIELD OF THE INVENTION

This invention relates to small particle characteristic determination.

BACKGROUND OF THE INVENTION

The use of detection devices for determination, or identification, of particle size is now well known, and such devices have been increasingly capable of determining particles of ever smaller size, including detection and determination of particles in fluids moved at ever increasing flow rates.

Particle detection utilizing scattering of light, such as laser light, in a sensing region, including positioning of the sensing region intracavity, is now commonly used for the detection of particles, and particularly small particles, such as submicron particles, with the light scattered by the particles at the sensing region being collected and detected and the size of the detected small particles being then determined from the size of the scattered light signals (see, for example, U.S. Pat. Nos. 4,571,079, 4,594,715, and 4,798,465).

A laser using an optically pumped, solid state laser medium, and, more particularly, a solid state laser medium, such as, for example, a Neodymium doped (1.1% by weight) Yttrium Aluminum Garnate (Nd:YAG) crystal, within the laser cavity and end-pumped by one or more laser diodes, such as one or more Gallium Aluminum Arsenide (GaAlAs) laser diodes, is shown, for example, in U.S. Pat. Nos. RE 34,729, 4,653,056, 4,723,257 1,739,507, 4,809,291 and 4,872,177, and use of a solid state laser, as above described, has been heretofore developed in conjunction with a sensing region within the laser cavity by Jon C. Sandberg.

Currently available commercial instrumentation based on laser light scattering provides only information on the size distribution and concentration of particles in the sample medium. There is increasing commercial interest, however, in instrumentation that can provide compositional information with respect to detected particles. Knowledge of the composition of detected particles can provide valuable guidance for identifying the source of the particles and/or allow prediction of the impact of a type of particle contamination on a critical manufacturing process. The interest in compositional information is sufficiently great that even rudimentary classification of particles into a few categories would be of significant commercial value.

Devices and/or methods are currently known that utilize lasers for illumination of particles in conjunction with fluorescence, for example, to enable detection of particles (see U.S. Pat. No. 4,281,924), and devices and/or methods are also currently known that utilize infrared emissions to enable identification of unknown chemical species (see U.S. Pat. No. 4,496,839), multi-point pyrometry-based compensated temperature sensing and detection (see U.S. Pat. No. 5,156,461), and analysis of solid material by laser heating of a thin surface layer of the solid material to cause thermal emissions of infrared radiation indicative of characteristics relating to the molecular composition of the solid material (see U.S. Pat. No. 5,075,552).

Thus, while devices and/or methods for detection and/or determination of particles utilizing light scattering, as well as devices and/or methods for heating various items to incandescence for detecting the items or characteristics thereof, are shown in the prior art, the devices and/or methods shown in the prior art are not directed, for example, to particle characteristic determination by detection of resulting light due to illumination of small optically absorbing particles by high intensity light, and/or detection of resulting light that includes both scattered light and emitted light due to heating of optically absorbing particles to a temperature at which a detectable level of incandescent light is emitted.

SUMMARY OF THE INVENTION

This invention provides particle characteristic determination. A sensing region, capable of having particles, including optically absorbing particles, thereat, receives high intensity light from a high intensity light source, such as a laser, and preferably a solid state laser, having a laser cavity with the sensing region within the laser cavity, so that the high intensity light contacting the small particles at the sensing region causes resulting light that includes elastically scattered light due to light contact with the small particles and emitted light due to heating to incandescence of the optically absorbing particles to cause detectable emission, or incandescence (as used herein, incandescence includes visible and/or invisible black body emission).

One or more optical detection units are utilized to enable predetermined particle characteristic determination, and a plurality of optical detecting units, each of which is capable of detecting predetermined portions of the resulting light from the sensing region, such as wavelength sensitive optical detecting units, including optical detecting units having an optical detector and an associated wavelength sensitive optical filter, can be used to sense the resulting light at the sensing region, with a detecting unit, or combinations of detecting units, enabling predetermined particle characteristic determination of the small particles, including detection of emitted light to provide outputs enabling at least temperature range indications, detection of scattered light to provide outputs enabling particle size and/or temporal characteristic indications, and/or detection of scattered light (or, at least in some cases, detection of emitted light) to provide outputs enabling particle position detection within the sensing region, with composition, or composition characteristic, determination being enabled through analysis of a plurality of optically absorbing particle characteristic determining outputs from the detecting units, and with such determination being further enabled by detection of power at the sensing region by an additional optical detecting unit.

It is therefore an object of this invention to provide an improved small particle determination device and method capable of improved small particle characteristic determination.

It is another object of this invention to provide a small particle characteristic determination device and method using a high intensity light source.

It is still another object of this invention to provide a small particle characteristic determination device and method utilizing particle incandescence.

It is still another object of this invention to provide a small particle determination device and method utilizing particle incandescence at a sensing region, with the device having a laser, such as a solid state laser, providing high intensity light within a laser cavity having the sensing region therein.

It is still another object of this invention to provide a small particle characteristic determination device and method using a high intensity light source at a sensing region having small particles, including optically absorbing particles, thereat to cause different detectable types of resulting light upon contact of the high intensity light with the small particle.

It is still another object of this invention to provide a small particle characteristic determination device and method utilizing a high intensity light source providing high intensity light at a sensing region having small particles, including optically absorbing particles, thereat whereby high intensity light contacting the small particles causes resulting light that includes emitted light due to heating of the absorbing particles to a temperature at which a detectable level of incandescent light is emitted with the emitted light terminating if vaporization of the optically absorbing particles occurs.

It is still another object of this invention to provide a small particle determination device and method utilizing a high intensity light source providing high intensity light at a sensing region having small particles, including optically absorbing particles, thereat whereby high intensity light contacting the small particles causes resulting light that includes elastically scattered light due to contact of the high intensity light with the small particles and emitted light due to heating of the absorbing particles to a temperature at which a detectable level of incandescent light is emitted.

It is another object of this invention to provide a small particle determination device and method utilizing a plurality of optical detecting units, each of which is capable of detecting predetermined portions of the resulting light from a sensing region, such as wavelength sensitive optical detecting units, including optical detecting units having a detector and an associated wavelength sensitive filter, whereby predetermined characteristics of the small particles can be determined by a detecting unit or a combination thereof.

It is another object of this invention to provide a small particle determination device and method utilizing a plurality of optical detecting units providing outputs different combinations of which enable predetermined particle characteristic determination, including particle size and/or position of the small particles, temperature range and/or vaporization characteristics of optically absorbing particles, and/or composition, or composition characteristics, of optically absorbing particles.

It is another object of this invention to provide a small particle determination device and method utilizing a plurality of optical detecting units to enable predetermined particle characteristic determination, including use of a portion of said plurality of optical detecting units to detect resulting light from a sensing region and a second portion of said plurality of optical detecting units to detect power at said sensing region.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which.

DESCRIPTION OF THE INVENTION

Figure 1:
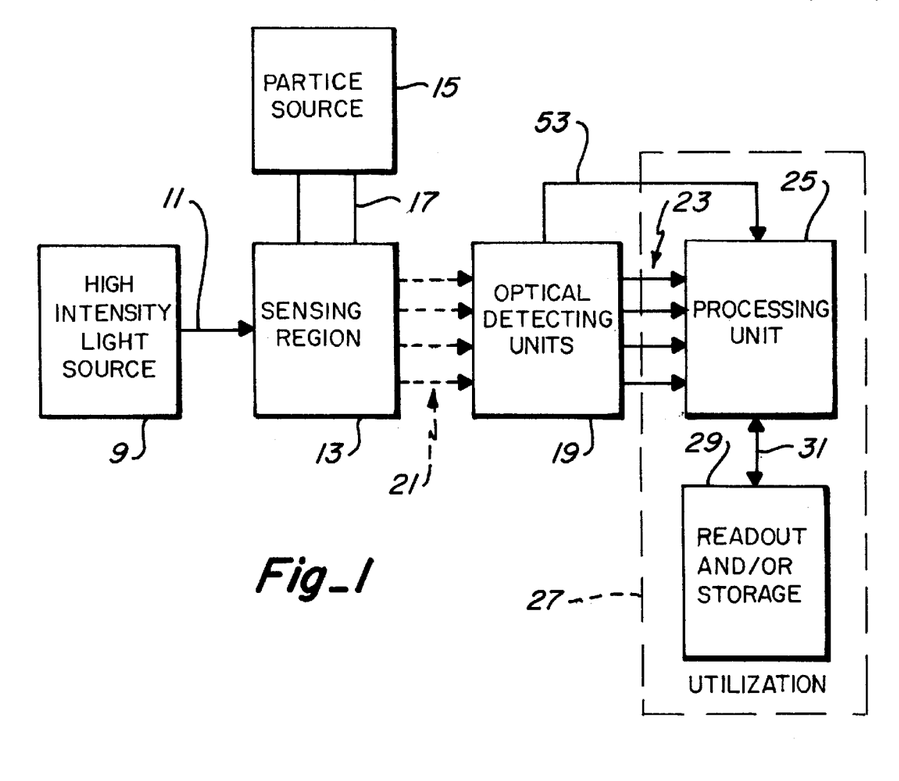
FIG. 1 is a block diagram generally illustrating the device of this invention.

As indicated in FIG. 1, high intensity light source 9 provides high intensity light 11, at a peak intensity, for example, greater than about $10^5$ Watts per square centimeter ($10^5$ W/cm$^2$), to sensing reunion 13 capable of having small particles, including optically absorbing particles, thereat, with the small particles including particles normally having a diameter in the range of about 0.05 microns to 10 microns.

As also indicated in FIG. 1, the small particles are normally provided to sensing region 13 from a particle source 15, such as, or from, an environment to be monitored, with the particles following free trajectories through a vacuum or with the particles being entrained in a fluid, such as a gaseous medium, and passed to the sensing region through conduit 17 at a selected flow rate, such as, for example, a flow rate of 0.01 CFM (cubic feet per minute).

The high intensity light 11 comes into contact with the small particles at sensing region 13 to cause resulting light that occurs due to elastic scattering of light by particle contact and heating of the optically absorbing particles to a temperature at which a detectable level of incandescent light is emitted so that the optically absorbing particles emit light with the resulting light terminating if vaporization of the small particles occurs.

A plurality of optical detecting units 19 sense the resulting light at sensing region 13 and resulting light, along paths 21, is detected to provide electrical signal outputs 23 indicative of selected, or predetermined, characteristics of the small particles, including particle size and/or composition of optically absorbing particles.

The electrical signal outputs are processed by processing unit 25 of a utilization unit 27 that normally includes readout and/or storage 29 connected to processing unit 25 through lead, or cable, 31. Processing unit 25 can be, or include, for example, a computer for processing, including analysis, using the various output signals, or a combination of output signals, from the detecting units, normally in conjunction with known characteristics of the small particles.

A laser, or laser system, is preferably utilized as the high intensity light source, and, as specifically shown in FIGS. 2, 4, 6, and 7, is a laser 9 providing laser light 11 at a sensing region 13 within the laser cavity 33. Laser 9 is preferably a continuous-wave, solid state laser having an optically pumped solid state laser medium 35 in a low loss optical resonator, or cavity, 33 that combines high intrinsic optical power generating capability (a power generating capability, for example, greater than about 100 mW (milliwatts)) with low optical losses necessary for efficient power buildup, and with the laser providing laser light 11 at sensing region 13 within the laser cavity at the very high peak intensity greater than $10^5$ Watts per square centimeter ($10^5$ W/cm$^2$).

Laser medium 35 may be, for example, a rare earth ion doped laser crystal, such as a Neodymium doped (1.1% by weight) Yttrium Aluminate Garnate (Nd:YAG) crystal, optically pumped by a high power laser diode 37, such as a Gallium Aluminum Arsenide (GaAlAs) laser dxode.

Small particles at sensing region 13 contacting the laser light at sensing region 13 within laser cavity 33 cause elastic scattering of the laser light and small particles having significant levels of optical absorption at the laser wavelength begin to heat rapidly to a temperature at which a detectable level of incandescent light is emitted.

As indicated in FIGS. 2, 4, 6, and 7, pump beam, or light, 39 from laser diode 37 is focused by lens 41 into laser medium 35 with laser medium 35 being within laser cavity 33 since the laser cavity is formed between coating 43 on the outer side (i.e., the side adjacent to lens 41) of the laser medium and mirror 45, such as an external concave mirror (the cavity opening, as shown, is 10 cm and the radius of concave mirror 45 is 17 cm). Laser cavity 33 is normally established for 1064 nm radiation with coating 43 passing pump light 39 from laser diode 37 at 808 nm. Coating 43 (which could be replaced by a mirror, such as a planar mirror) and mirror 45 are configured to have high reflectance at 1064 nm, and coating 43 also has high transmission at the pump wavelength of 808 nm.

When pumped with approximately 500 mW of 808 nm light from the laser diode, the cavity lases at 1064 nm in a TEM$_{00}$ mode with approximately 1 kW of circulating power, and with a beam radius in the cavity of approximately 220 microns, a peak laser intensity exceeding $5 \times 10^5$ W/cm$^2$ is realized.

As also indicated in FIGS. 2, 4, 6, and 7, sensing region 13 is positioned substantially about equidistant between laser medium 35 and mirror 45, and can, for example, have small particle-containing fluid injected into the sensing region through airjet 47. In addition, intracavity power can be monitored, or sampled, by coupling the small amount of power passed through mirror 45 through lens 49 to detector 51 providing an intracavity power output signal to processing unit 25 through lead 53.

As also more specifically indicated in FIGS. 2, 4, 6, and 7, each of the optical detecting units 19 is wavelength sensitive and now preferably includes a lens 55 for focusing resulting light from sensing region 13 to detector 57 through associated filter 59 (other arrangements might be utilized, however, so long as the optical detecting units are capable of detecting predetermined portions of the resulting light from the sensing region and provide outputs indicative thereof). As brought out herein, the resulting light detected by detectors 57 enables predetermined particle characteristic determination of the small particles that can include determination of particle size and/or determination of composition with respect to the optically absorbing particles.

As indicated, detecting units 19 are positioned about, or around, sampling region 13 to sense and collect the resulting light (the resulting light, as brought out above, includes scattered light, or radiation, and incandescent light, or radiation, emitted due to heating of the optically absorbing small particles). Quantitative characterization of the magnitude of the scattered laser radiation and the magnitude and/or spectral properties of the incandescent radiation allow classification of the particles according to composition of the particles.

Figure 2:
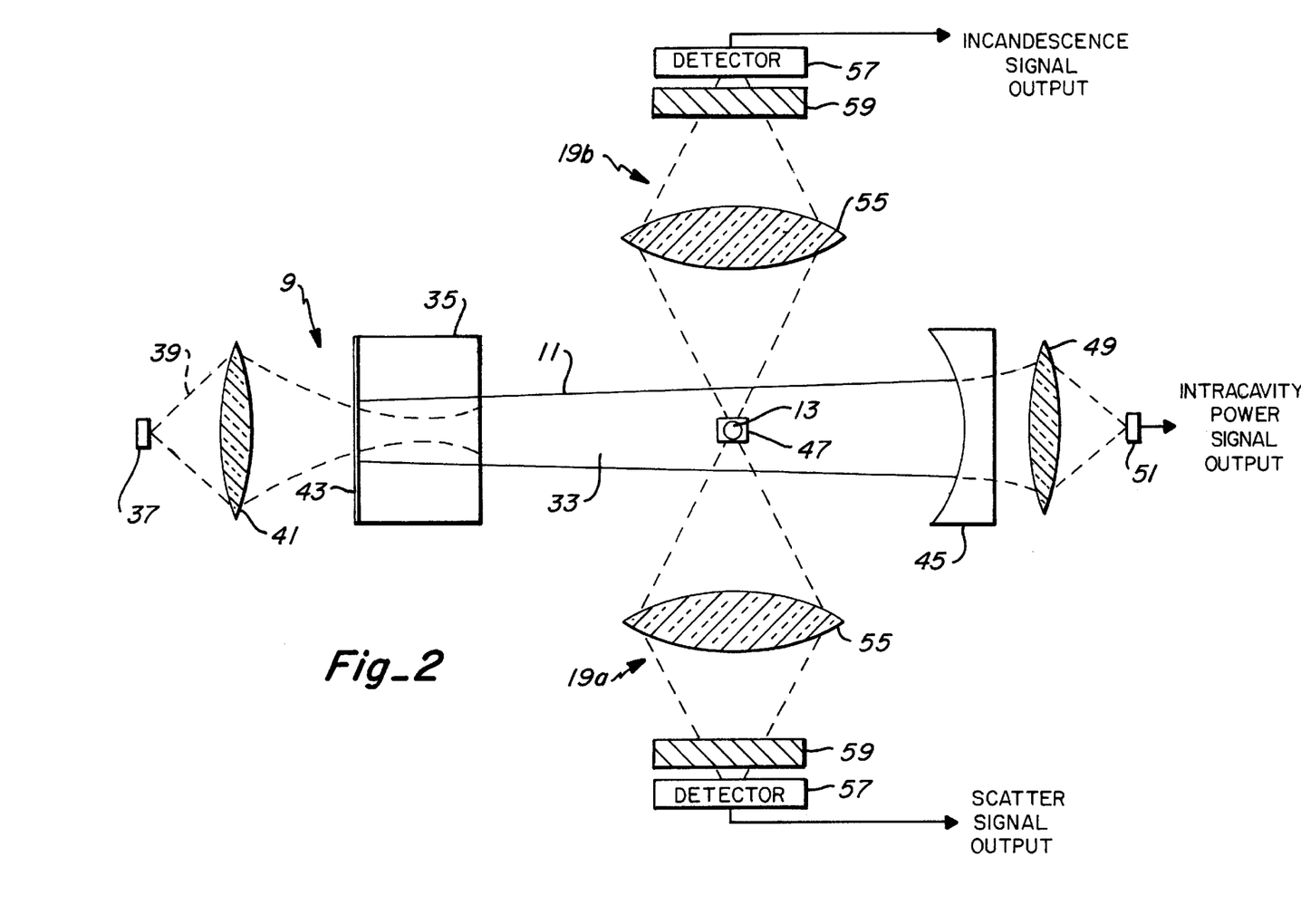
FIG. 2 is a simplified side view illustrating the device of this invention generally illustrated in FIG. 1 and having a pair of detecting units.

With particular respect to FIG. 2, a pair of optical detecting units 19 (designated as optical detecting units 19a and 19b in FIG. 2) are positioned to detect resulting light emitted from sensing region 13. Optical detecting unit 19a is in a channel designated as the scatter channel, and optical detecting unit 19b is in a channel designated as the incandescence channel.

Optical detecting unit 19a in the scatter channel, as shown in FIG. 2, has a detector 57, preferably a silicon photodiode (all of the detectors illustrated in FIGS. 2, 4, 6, and 7 could be silicon detectors), positioned to receive light through associated filter 59, such as Schott RG850 filter glass, designed to be sensitive primarily to scattered light at 1064 nm to give an overall detection wavelength band of between about 850 nm and 1150 nm (while there is incandescent emission in this band, it has been found to be much smaller than that of the scattered light and of no significant influence). Particle size can be determined, for example by a processing unit such as shown in U.S. Pat. No. 4,571,079 or, for greater sensitivity, by a process unit as shown in U.S. Pat. No. 4,798,465.

Optical detecting unit 19b in the incandescence channel, as also shown in FIG. 2, has a detector 57 positioned to receive light through associated filter 59, such as Schott KG5 filter glass, designed to be sensitive in about the 300 nm to 780 nm wavelength range (no significant influence of scattered radiation on the incandescence channel has been found, just as likewise, no significant influence of incandescent radiation on the scatter channel has been found).

FIGS. 3A through 3D are graphs depicting data utilizing the device of this invention as illustrated in FIG. 2. While the data depicted in FIGS. 3A through 3D has been scaled arbitrarily for clearer presentation, the ratios of the scatter and incandescent signal sizes have been preserved.

Figure 3A:
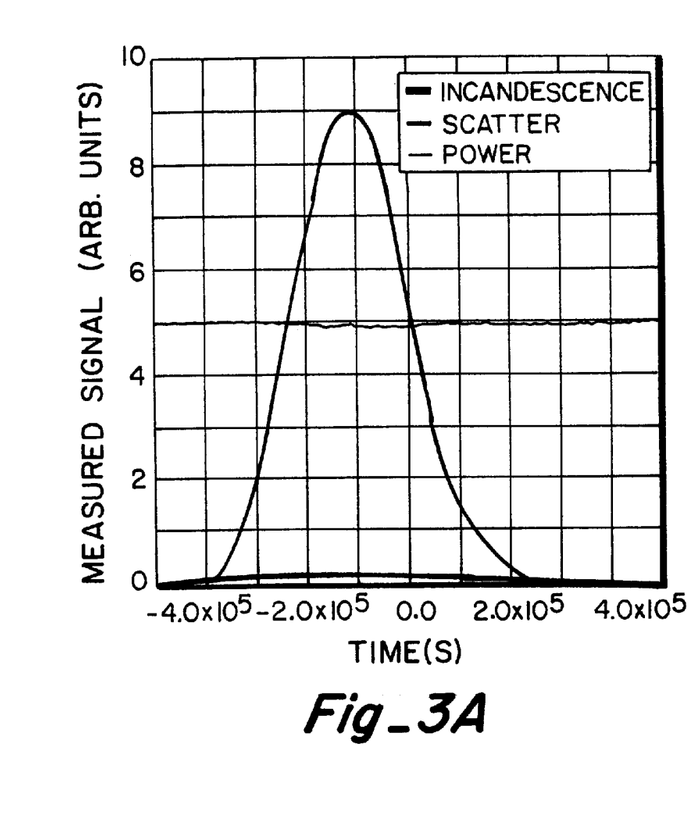
FIGS. 3A through 3D are graphs illustrating typical outputs provided by the device of this invention as illustrated in FIG. 2.

FIG. 3A depicts a typical signal for an optically non-absorbing small standard particle (a 0.305 micron PSL (polystyrene latex monosphere) particle). The scatter signal depicted is a Gaussian temporal profile of the particle moving through a TEM$_{00}$ laser beam, wiith a Gaussian width of approximately 26 microseconds FWHM (full width at half maximum), which is consistent with the beam and airjet dimensions utilized and a sample flow rate of 0.01 CFM. There is no detectable signal on the incandescence channel.

Figure 3B:
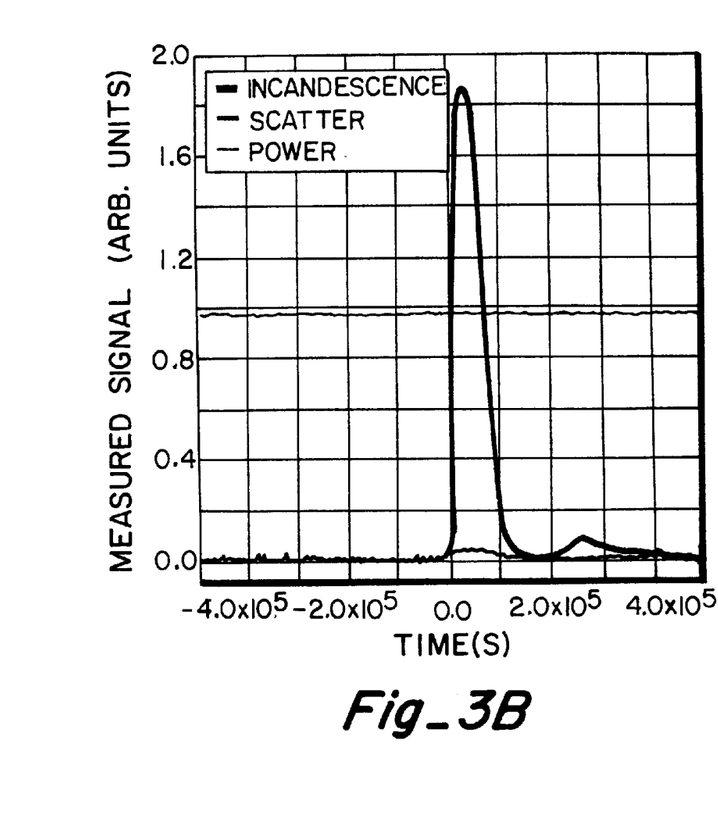

FIG. 3B depicts a typical signal for a carbon particle. Carbon is known to be highly optically absorbing at the laser wavelength utilized, and this results in two conspicuous features in the observed signals. First, carbon particles produce easily detectable incandescent signals since the ratio of incandescent signal size to scatter signal size for carbon exceeds that of PSL by at least a factor of 2000 for particles in the 0.2 to 0.3 micron diameter range. Second, under conditions of identical geometry and flow rates, carbon particles produce scatter signals that are approximately 9.8 microseconds FWHM (a facto), of 2.8 shorter than PSL), and have distinct non-Gaussian features. The shorter pulses are taken as an indication that carbon particles are heated to a temperature at which they vaporize before passing completely through the beam.

Figure 3C:
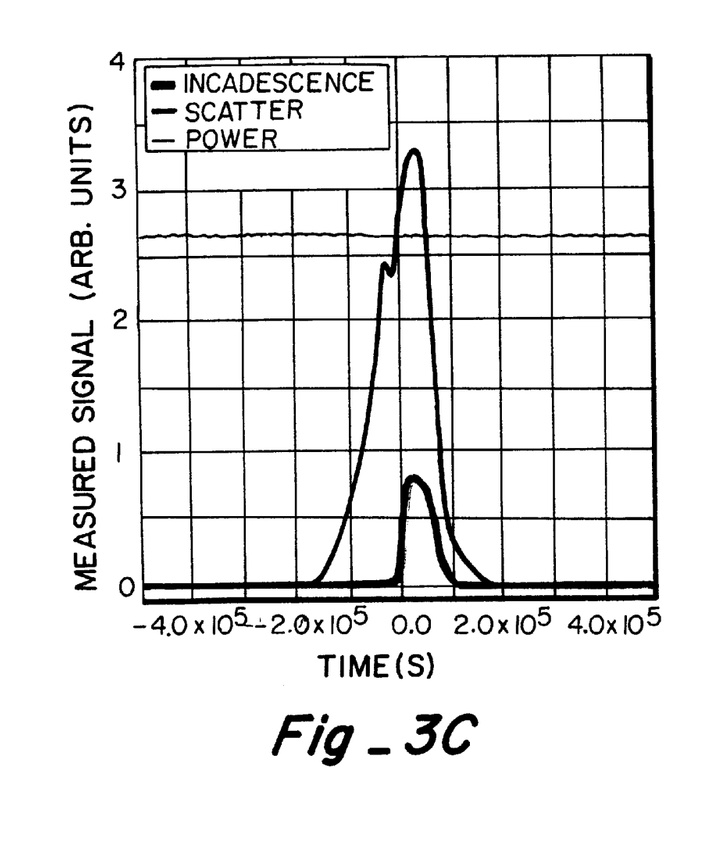

FIG. 3C depicts a typical signal for a silicon particle. Silicon is also known to be optically absorbing at the laser wavelength utilized and produces signals qualitatively similar to that of carbon. The scatter pulses are shorter than PSL, indicating particle vaporization, and incandescent signals are easily detectable. The most prominent difference between silicon and carbon is that the ratio of incandescent to scatter signal sizes is a factor of approximately 150 times smaller.

Figure 3D:
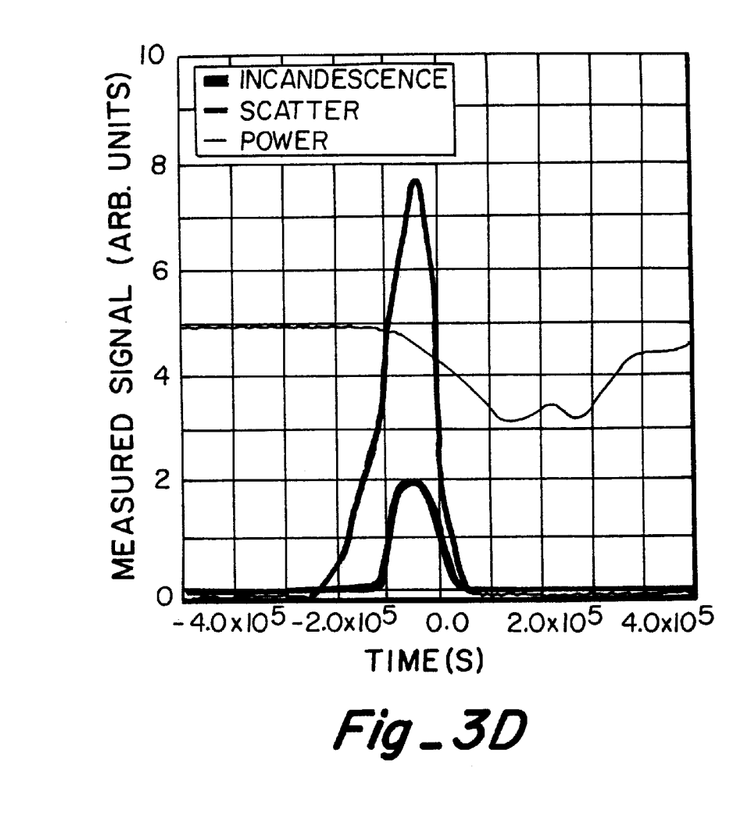

FIG. 3D depicts a typical signal for a nickel particle. Nickel is observed to produce signals very similar to silicon, with one significant exception, namely, that nickel particles produce a very noticeable effect on the intracavity power, with the intracavity power showing a pronounced drop that occurs mostly after the particle is vaporized. This effect is not observed with silicon.

With respect to the above observations, the PSL particle is essentially optically non-absorbing and produces a signal typical of most intracavitny light scattering devices. The optically absorbing particles, on the other hand, all show indications of bring vaporized before completely passing through the light beam at the sensing region.

Under conditions of being completely vaporized (which might, or might not, occur for the optically absorbing particles at the sensing region), (all particles of a given material should reach similar temperatures, with these temperatures being correlated with the boiling point of the material, carbon ($T_b$=5100 K) showing the strongest incandescent signal. Silicon and nickel have similar boiling points ($T_b$=2560 K and $T_b$=3005 K, respectively) and produce similar size incandescent signals for similar sized particles (the particle size being inferred from the magnitude of the scatter signal).

While the drop in intracavity power observed with nickel is not currently understood, it indicates another composition specific feature that may be used to empirically discriminate between different types of small particles.

Figure 4:
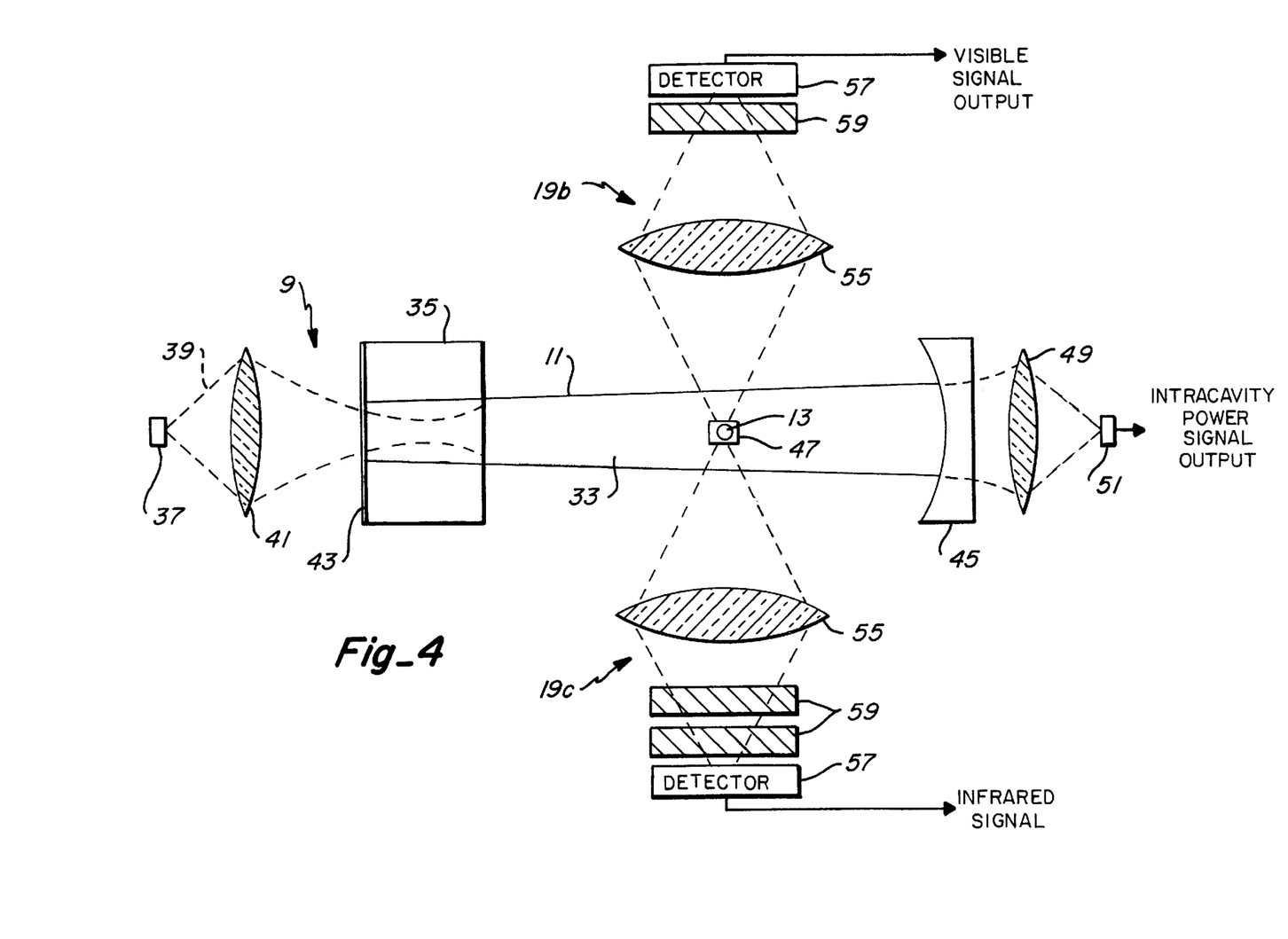
FIG. 4 is a simplified side view similar to that illustrated in FIG. 2 but having a pair of detecting units one of which is different from the detecting units illustrated in FIG. 2.

With particular respect to FIG. 4, the laser is the same as shown in FIG. 2, but the resulting light emitted from the sensing region, is collected by first and second optical detecting units that are both intended for detection of incandescent emission. As indicated, optical detecting unit 19b is in a channel designated as the visible channel, while optical detecting unit 19c is in a channel designated as the infrared channel.

Optical detecting unit 19b in the visible channel, as shown in FIG. 4, includes a detector 57 having an associated filter 59, such as Schott KG5 filter glass, in the optical path between the detector and the sensing region so that the visible channel is sensitive to about the 300 nm to 780 nm wavelength range, while optical detecting unit 19c in the infrared channel includes a detector 57 having an associated filter 59 that includes two different sections, such as Schott KG5 filter glass and Schott RG715 filter glass, in the optical path so that the infrared channel is sensitive to about the 680 nm to 780 nm wavelength range.

The device of the invention, as shown in FIG. 4, is not sensitive to optically non-absorbing particles, but the magnitudes of the two signals provide a degree of direct measurement capability for the temperature of incandescing small optically absorbing particles. The relative magnitudes can be used to determine the temperature of the optically absorbing particle responsible for incandescent emission (it is to be realized that the number and/or configuration of the optical detecting units utilized could be modified, as needed, and also could be made to be responsive to different and/or additional wavelength ranges that do not necessarily overlap). Knowledge of the filter transmissions, detector spectral responsivity, and spectral properties of incandescent emission can be used to determine a temperature from an observed ratio of visible to infrared channel signal sizes.

Figure 5:
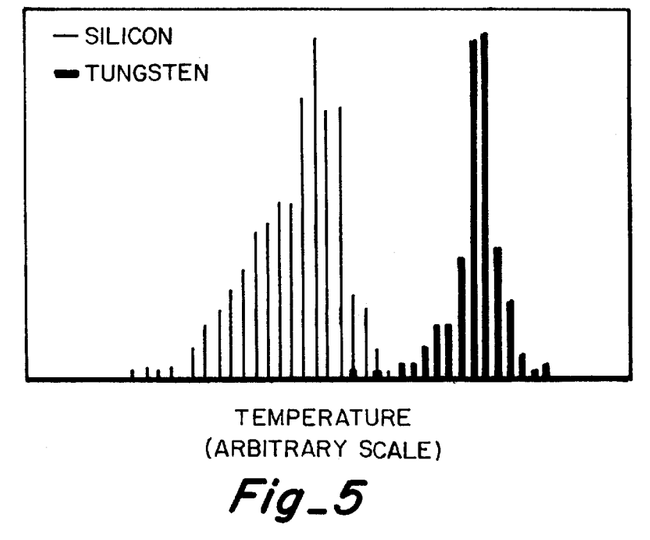
FIG. 5 is a graph illustrating processed raw outputs utilizing the device of this invention as illustrated in FIG. 4.

FIG. 5 depicts typical processed data collected for silicon and tungsten particles with the device of this invention as illustrated in FIG. 4. As can be appreciated from FIG. 5, the silicon and tungsten particles fall into distinct categories when their signals are processed to yield approximate values for the temperature of the particles responsible for the observed incandescent emission. The categories are separated in the expected manner, with tungsten particles producing higher observed temperatures than silicon in accordance with the higher known boiling point of tungsten.

Figure 6:
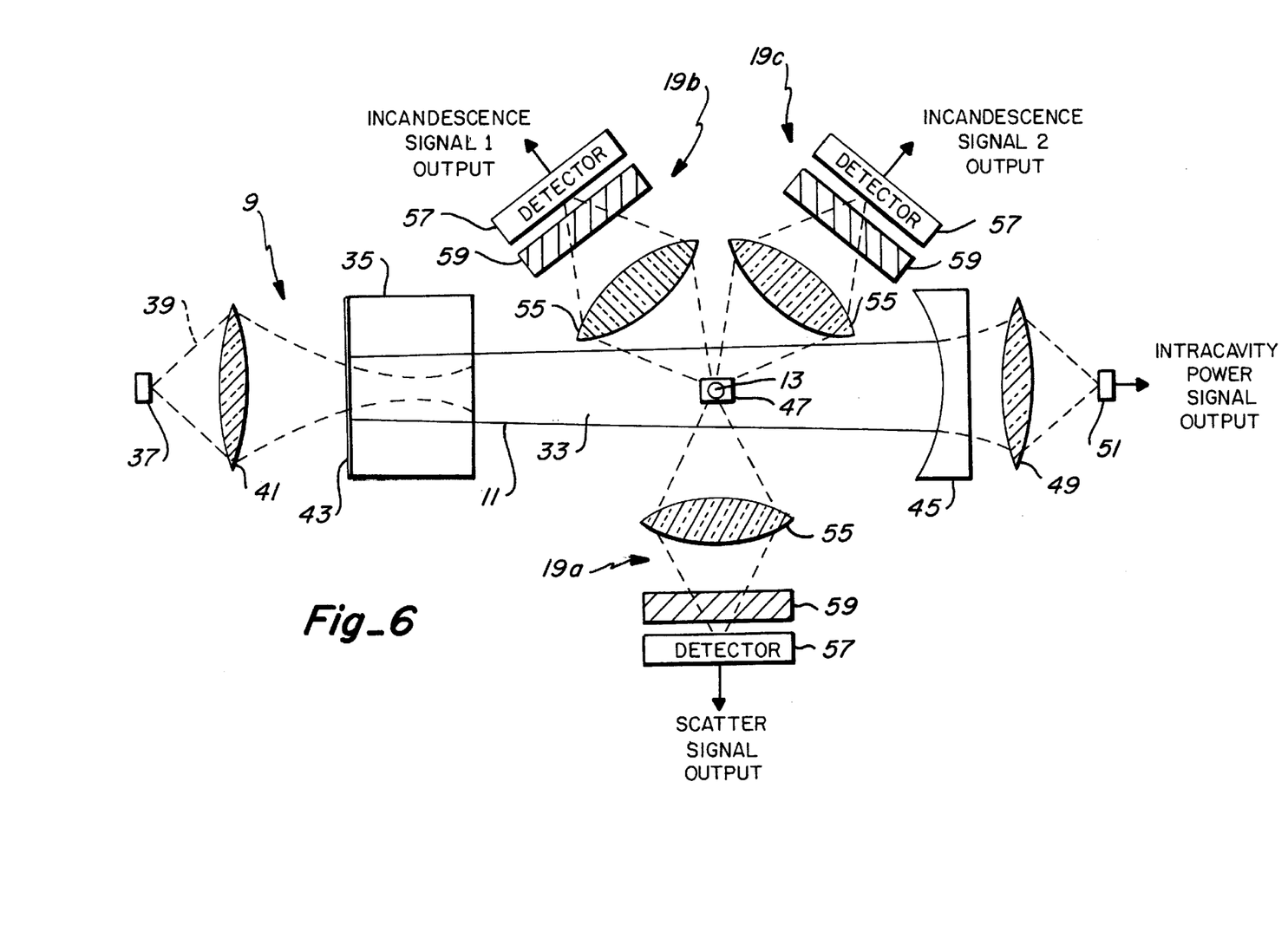
FIG. 6 is a simplified side view illustrating the device of this invention similar to that showing in FIGS. 2 and 4 but utilizing three detecting units.

With particular respect to FIG. 6, the laser is the same as shown for FIGS. 2 and 4, but the detection system has been modified to use three optical detecting units (designated as optical detecting units 19a, 19b, and 19c in FIG. 6) in three different channels. As shown, these optical detecting units are a combination of the optical detecting units shown in FIGS. 2 and 4 (the optical detecting unit in the incandescence channel, as shown in FIG. 2, is like the optical detecting unit in the visible channel, as shown in FIG. 4).

As can be appreciated from the above description with respect to FIGS. 2 and 4, the incandescent channels (designated as visible and infrared channels in FIGS. 4 and 6) incorporate suitable elements to make the optical detecting unit in each channel wavelength sensitive, such as by including, as shown, an optical filter and an optical detector in each optical detecting unit, so that the relative magnitudes of the two signals permit determination of temperature of an incandescing small optically absorbing particle, while the scatter channel measures scattered radiation and is designed to determine the total magnitude of the scattered radiation for size determination of both optically absorbing and optically non-absorbing small particles.

Figure 7:
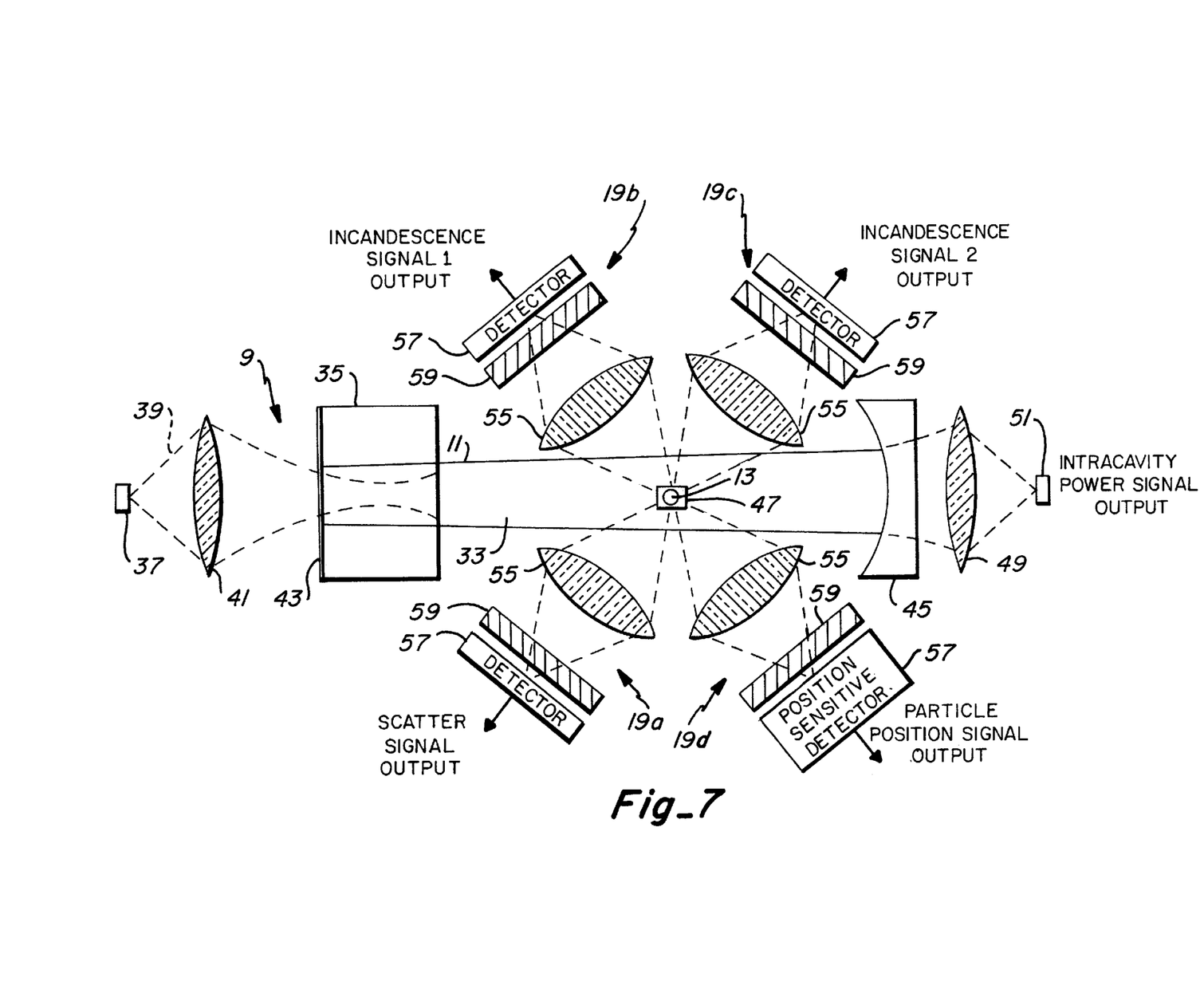
FIG. 7 is a simplified side view illustrating the device of this invention like that shown in FIG. 6 but including a fourth detecting unit.

With particular respect to FIG. 7, the device of this invention, as shown, is identical to that of FIG. 6 except for adding a fourth optical detecting unit (designated as optical detecting unit 19d in FIG. 7). Optical detecting unit 19d is in a channel designated as the particle position channel that is designed so that analysis of the temporal characteristics of the signal can be used to verify whether, and if, an optically absorbing particle has been vaporized before leaving the sensing region.

As specifically indicated in FIG. 7, optical detecting unit 19d is similar to scatter channel optical detecting unit 19a except that the scatter signal, passed through lens 55 and filter 59, is received by a spatially, or position, sensitive detector 57 (i.e., a split detector) so that the intensity of scattered radiation as a function of particle position as it moves through the light beam in the sensing region can be monitored (while not shown, the position detector could, in at least some instances, receive emitted light, rather than scattered light, and still function in the same manner).

A spatially sensitive detector is useful in that, while the boiling point of the material is the most important factor in determining observed particle temperatures, mathematical models of the vaporization process predict other factors such as absorption depth in the material will also affect particle temperatures, and these factors will also affect the physical position in the laser beam at which particle vaporization starts to occur. Direct measurement of this position allows some correction for these additional factors and consequently a more accurate determination of the boiling point for the particle.

In addition, elastically scattered light indicative of the size of the small particles and the intensity of the light source at the position of the small particles can be detected by an optical unit, as above, with the optical detection unit providing an output that is indicative of at least one of the magnitude of the elastically scattered light and the position of the small particles within the sensing region, providing temporal characteristic information. A processing unit is utilized to receive the output from the optical detection unit and, based upon one or more temporal characteristics of the received output (such as, for example pulse width), enables predetermined characteristic determination, other than particle size, of the small particles.

As described above, this invention results in a device and method that is both reliable and cost effective; generates high intensity light that is provided at the sensing region; generates high light intensities greater than $10^5$ W/cm$^2$ with high total optical power (greater than 100 mW); detects incandescent emission from small particles as an indication of optical absorption; detects small particles, including absorbing particles, using resulting light including scattered light and emitted light due to incandescence of absorbing particles to provide size and composition outputs; uses the magnitude or spectral content of incandescent emission from small particles as a measurement of vaporization temperature of an absorbing particle; uses vaporization temperature of an absorbing particle as an indicator of particle composition; measures temporal composition specific features, or characteristics (such as pulse width), of a particle light scattering signal as an indicator of particle vaporization; uses a spatially sensitive light detector for resulting light to provide an indicator for the spatial position at which the absorbing particle begins to vaporize; monitors laser power during particle passage for determining composition specific features; and/or uses the foregoing in conjunction with a laser, preferably a solid state laser.

As can be appreciated from the foregoing, this invention therefore provides an improved device and method for small particle characteristic determination.

What is claimed is:

1. A device for small particle characteristic determination, said device comprising:

a region capable of having the small particles thereat with at least a portion of the small particles being optically absorbing particles;

a high intensity laser light source including a laser cavity having said region within said laser cavity, said high intensity laser light source providing laser light at said region for contact with the small particles thereat to cause heating of said optically absorbing particles to incandescence at said region to cause resulting light to be emitted from within said region where said heating occurs with said resulting light being indicative of said heating to incandescence of said optically absorbing particles; and at least one optical detecting unit for sensing said resulting light emitted from within said region where said heating occurs thereby enabling predetermined particle characteristic determination, other than size determination, of the small particles.

2. The device of claim 1 wherein said high intensity laser light source provides a peak intensity greater than about $10^5$ W/cm$^2$ at said region.

3. The device of claim 1 wherein said high intensity laser light source also includes a solid state laser having a laser medium optically pumped by a laser diode with said laser medium being within said laser cavity.

4. The device of claim 1 wherein said device also includes a power detector for detecting the power at said region.

5. The device of claim 1 wherein said device includes a plurality of optical detecting units which is wavelength sensitive.

6. The device of claim 5 wherein each of said plurality of wavelength sensitive optical detecting units includes a wavelength sensitive filter and a detector with said detector receiving a portion of said resulting light through said filter.

7. The device of claim 5 wherein different ones of said optical detecting units provide outputs based upon predetermined portions of said resulting light emitted by incandescence of said optically absorbing particles at said region.

8. The device of claim 7 wherein said outputs based upon said resulting light emitted by incandescence enable temperature range determination of said optically absorbing particles as said predetermined particle characteristic determination.

9. The device of claim 1 wherein said resulting light terminates upon vaporization of said optically absorbing particles to thereby enable temperature determination with respect to said optically absorbing particles as at least a portion of said predetermined particle characteristic determination of the small particles.

10. The device of claim 1 wherein said device also includes a conduit through which the small particles are passed into said region.

11. The device of claim 1 wherein said device also includes a processing unit connected with said at least one optical detecting unit and, responsive to receipt of an output therefrom, providing said particle characteristic determination of the small particles.

12. The device of claim 1 wherein the small particles have a diameter of between about 0.05 microns and 10 microns.

13. A device for small particle characteristic determination, said device comprising:

a sensing region capable of having the small particles thereat with at least a portion of the small particles being optically absorbing particles;

a high intensity laser light source providing light at said sensing region for contact with the small particles thereat to cause resulting light at said sensing region that includes both light elastically scattered by the small particles at said sensing region and light emitted due to incandescence of said optically absorbing particles at said sensing region; and a plurality of optical detecting units each receiving said resulting light with at least a first one of said plurality of optical detecting units detecting said resulting light elastically scattered by the small particles and providing an output indicative of said light elastically scattered by the small particles, and with at least a second one of said plurality of optical detecting units detecting said resulting light emitted due to incandescence of said optically absorbing particles and providing an output indicative of said light emitted due to incandescence of said optically absorbing particles, said first one and said second one of said plurality of detecting units being capable of concurrent detection of said resulting light and the outputs of said plurality of optical detecting units enabling predetermined particle characteristic determination of the small particles.

14. The device of claim 13 wherein said plurality of optical detecting units includes a first optical detecting unit for detecting said light elastically scattered by the small particles and at least second and third optical detecting units for detecting said light emitted due to incandescence of said optically absorbing particles.

15. The device of claim 14 wherein said at least second and third optical detecting units detect said light emitted due to incandescence of said optically absorbing particles within different wavelength ranges to enable said predetermined particle characteristic determination.

16. The device of claim 15 wherein said second optical detecting unit detects said light emitted due to incandescence of said optically absorbing particles within a visible light wavelength range, and wherein said third optical detecting unit detects said light emitted due to incandescence of said optically absorbing particles within an infrared light wavelength range.

17. The device of claim 14 wherein said plurality of optical detecting units includes a fourth optical detecting unit for detecting positioning of the small particles within said sensing region.

18. The device of claim 13 wherein said device includes a power detector for detecting power at said sensing region and providing an output indicative thereof to said processing unit.

19. A device for small particles characteristic determination, said device comprising:
- a sensing region capable of having the small particles thereat with at least a portion of the small particles being optically absorbing particles;
- a laser light source having a laser cavity with laser light therein, said sensing region being within said laser cavity, and said laser light contacting the small particles in said sensing region to cause heating of said optically absorbing particles to incandescence to cause resulting light to be emitted indicative of said heating to incandescence of said optically absorbing particles; and
- at least one optical detecting unit for sensing said resulting light emitted due to heating of said optically absorbing particles to incandescence at said sensing region and responsive thereto providing outputs enabling predetermined particle characteristic determination of the small particles.

20. The device of claim 19 wherein said laser light source includes a solid state laser having a rare earth ion doped laser crystal as a laser medium within said laser cavity.

21. The device of claim 20 wherein said crystal is a Nd:YAG crystal.

22. The device of claim 20 wherein said laser light source also includes a high power laser diode for optically pumping said crystal.

23. The device of claim 22 wherein said laser diode is a GaAlAs laser diode.

24. The device of claim 19 wherein said device includes a plurality of optical detecting units, and wherein said at least one optical detecting unit includes a detector and a wavelength sensitive filter connected with said detector so that said filter determines passage of said resulting light to said detector.

25. The device of claim 19 wherein said device includes a power detecting unit for detecting intracavity power within said laser cavity.

26. The device of claim 25 wherein said power detecting unit includes an optical detector.

27. A device for small particle characteristic determination, said device comprising:
- a sensing region capable of having the small particles thereat with at least a portion of the small particles being optically absorbing particles;
- a high intensity laser light source for providing light at said sensing region with said light being elastically scattered at said sensing region by the small particles thereat and with said light also heating said optically absorbing particles at said sensing region to produce incandescence resulting in emitted light at said sensing region;
- a first wavelength sensitive optical detecting unit receiving said light from said sensing region and including a first detector for detecting at least a portion of said light received by said first wavelength sensitive optical detecting unit and providing an output indicative of said light elastically scattered by the small particles at said sensing region;
- a second wavelength sensitive optical detecting unit receiving said light from said sensing region and including a second detector for detecting at least a portion of said light received by second wavelength sensitive optical detecting unit, said second detector being capable of detection of said light concurrently with detection of said light by said first detector and providing an output indicative of said emitted light due to said incandescence of said optically absorbing particles; and
- a processing unit for receiving said outputs from said first and second wavelength sensitive optical detecting units and, responsive thereto, providing predetermined particle characteristic determination of the small particles.

28. The device of claim 27 wherein said emitted light terminates upon vaporization of said optically absorbing particles, and wherein said second wavelength sensitive optical detecting unit senses said termination of said emitted light upon vaporization of said optically absorbing particles and, responsive thereto, provides an indication thereof to said processing unit to enable said processing unit to determine temperature at vaporization with respect to said optically absorbing particles as at lea t a portion of said predetermined particle characteristic determination of the small particles.

29. The device of claim 27 wherein said first wavelength sensitive optical detecting unit includes a first wavelength sensitive filter connected with said first detector to pass to said first detector said light elastically scattered by the small particles at said sensing region, and wherein said second wavelength sensitive optical detecting unit includes a second wavelength sensitive filter connected with said second detector to pass to said second detector said emitted light due to incandescence of said optically absorbing particles received from said sensing region.

30. The device of claim 29 wherein said first filter passes light within a range of about 850 nm to 1150 nm, and wherein said second filter passes light within a range of about 300 nm to 780 nm.

31. A device for small particle characteristic determination, said device comprising:
- a sensing region capable of having the small particles thereat with at least a portion of the small particles being optically absorbing particles;
- a high intensity laser light source that includes a laser cavity with laser light therein and with said sensing region being within said laser cavity, said laser light at said sensing region being elastically scattered by the small particles and with said laser light at said sensing region heating said optically absorbing particles to produce incandescence resulting in emitted light;
- a first wavelength sensitive optical detecting unit receiving light from said sensing region and including a first detector that provides an output indicative of said light elastically scattered by the small particles at said sensing region;
- a second wavelength sensitive optical detecting unit receiving light from said sensing region and including a second detector that provides an output indicative of said emitted light due to said incandescence of said optically absorbing particles; and a processing unit for receiving said outputs from said first and second wavelength sensitive optical detecting units and, responsive thereto, providing predetermined particle characteristic determination of the small particles.

32. The device of claim 31 wherein said device also includes a power detecting unit for detecting the intracavity power at said laser cavity and providing an output indicative thereof to said processing unit.

33. A device for determination of optically absorbing small particle temperature characteristics, said device comprising:

a sensing region capable of having the optically absorbing particles thereat;

a high intensity laser light source having a laser cavity with laser light therein, said sensing region being within said laser cavity whereby said laser light heats the optically absorbing particles at said sensing region to produce incandescence resulting in emitted light;

a spectrally responsive detector receiving said light emitted at said sensing region and providing outputs indicative of the spectral variations of said emitted light; and a processing unit for receiving said outputs from said spectrally responsive detector and, responsive thereto, providing an output indicative of predetermined temperature characteristics of the optically absorbing particles at said sensing region.

34. The device of claim 33 wherein said emitted light terminates upon vaporization of the optically absorbing particles, and wherein said spectrally responsive detector senses said termination of said emitted light upon vaporization of the optically absorbing particles and, responsive thereto, provides an indication thereof to said processing unit to enable said processing unit to provide said output indicative of said predetermined temperature characteristics of the optically absorbing particles at said sensing region.

35. The device of claim 33 wherein said spectrally responsive detector includes first and second wavelength sensitive optical detecting units to provide said outputs from said spectrally responsive detector.

36. The device of claim 35 wherein said first wavelength sensitive optical detecting unit passes light between about 300 nm to 780 nm, and wherein said second wavelength sensitive optical detecting unit passes light between about 680 nm to 780 nm.

37. A device for small particle characteristic determination, said device comprising:

a sensing region capable of having the small particles thereat with at least a portion of the small particles being optically absorbing particles;

a high intensity laser light source for providing light at said sensing region with said light being elastically scattered at said sensing region by the small particles thereat and said light also heating said optically absorbing particles at said sensing region to a temperature at which a detectable level of incandescent light is emitted at said sensing region;

a first optical detecting unit receiving said light from said sensing region, said first optical detecting unit including a first detector for detecting at least a portion of said light received by said first optical sensing unit and providing an output indicative of said elastically scattered light within a first wavelength range;

a second optical detecting unit receiving said light from said sensing region, said second optical detecting unit including a second detector for detecting at least a portion of said light received by said second optical detecting unit, said second detector being capable of detection of said light concurrently with detection of said light by said first detector and providing an output indicative of said emitted light within a second wavelength range;

a third optical detecting unit receiving said light from said sensing region, said third optical detecting unit including a third detector for detecting said light received by said third optical detecting unit, said third detector being capable of detection of said light concurrently with detection of said light by said first and second detectors and providing an output indicative of said emitted light within a third wavelength range; and a processing unit for receiving said outputs from said first, second, and third optical detecting units and, responsive thereto, providing an output indicative of particle characteristics of the small particles, including particle size and composition of said optically absorbing particles.

38. The device of claim 37 wherein said device includes a fourth optical detecting unit receiving light from said sensing region, said fourth optical detecting unit including a fourth detector, with said fourth detector being a position sensitive detector that provides an output indicative of position of the small particles.

39. The device of claim 38 wherein each of said first, second, third, and fourth optical detecting units includes a wavelength sensitive filter.

40. The device of claim 39 wherein said first and fourth optical detecting units are wavelength sensitive within a wavelength range of about 850 nm to 1150 nm, wherein said wavelength sensitive detecting unit is wavelength sensitive within a wavelength range of about 300 nm to 780 nm, and wherein said third wavelength sensitive optical detecting unit is wavelength sensitive within a wavelength range of about 680 nm to 780 nm.

41. The device of claim 37 wherein said emitted light terminates upon vaporization of said optically absorbing particles, and wherein at least one of said second and third optical detecting units senses said termination of said emitted light upon vaporization of said optically absorbing particles and, responsive thereto, provides an indication thereof to said processing unit to enable said processing unit to determine temperature at vaporization with respect to said optically absorbing particles for use, at least in part, in determining said composition of said optically absorbing particles.

42. A device for small particle characteristic determination, said device comprising:

a sensing region capable of having the small particles thereat;

a high intensity light source having a known spatial intensity profile and providing light at said sensing region for contact with said small particles thereat to cause elastic scattering of light that is indicative of the size of the small particles and the intensity of said light from said light source at the position of the small particles, providing temporal characteristic information;

an optical detection unit for receiving said elastically scattered light and, responsive thereto, providing an output that is indicative of at least one of the magnitude of the elastically scattered light and the position of the small particles within said sensing region; and a processing unit for receiving said output from said optical detection unit and, based upon said temporal characteristic information, enabling predetermined characteristic determination, other than particle size, of the small particles.

43. The device of claim 42 wherein sail said temporal characteristic information is pulse width.

44. A method for small particle characteristic determination, said method comprising:
 providing the small particles at a sensing region with at least a portion of the small particles being optically absorbing particles;
 providing a laser having a laser cavity with laser light therein and establishing said sensing region within said laser cavity for contact of said laser light with the small particles thereat to cause heating of said optically absorbing particles to incandescence to cause resulting light within said sensing region that includes light emitted due to incandescence of said optically absorbing particles;
 sensing said resulting light emitted at said sensing region and providing outputs indicative thereof; and
 utilizing said outputs to provide predetermined particle characteristic determination with respect to at least aid optically absorbing particles.

45. The method of claim 44 wherein said method includes providing said laser light at said sensing region at a peak intensity greater than about $10^5$ W/cm$^2$.

46. The method of claim 44 wherein said method includes detecting the intracavity power within said laser cavity.

47. The method of claim 44 wherein said method includes detecting said resulting light due to incandescence of said optically absorbing particles within different wavelength ranges to enable said predetermined particle characteristic determination of said optically absorbing particles.

48. The method of claim 47 wherein said method includes determining temperature range indications from said detection of said resulting light due to incandescence of said optically absorbing particles as said predetermined particle characteristic determination of said optically absorbing particles.

49. The method of claim 47 wherein said different wavelength ranges are selected to be about 300 nm to 780 nm and 680 nm to 780 nm.

50. The method of claim 47 wherein said method also includes causing said resulting light to include light elastically scattered by the small particles at said sensing region.

51. The method of claim 50 wherein said method includes detecting said resulting light elastically scattered by the small particles within a wavelength range of about 850 nm to 1150 pm, and detecting said resulting light emitted by said optically absorbing particles within a wavelength range of about 300 nm to 780 nm.

52. The method of claim 51 wherein said method includes detecting said resulting light emitted by said optically absorbing particles within at least two different wavelength ranges.

53. The method of claim 52 wherein said method includes detecting said resulting light emitted by said optically absorbing particles within visible light wavelengths and within infrared light wavelengths.

54. The method of claim 44 wherein said method also includes detecting the position of the small particles within said sensing region and utilizing said position in providing said predetermined characteristic determination of said optically absorbing particles.

55. The method of claim 44 wherein the small particles are entrained in a fluid, and wherein said method includes passing said fluid through said sensing region at a predetermined flow rate.

56. The method of claim 44 wherein said method includes detecting the small particles having a diameter of between about 0.05 microns and 10 microns.

57. A device for small particle characteristic determination, said device comprising:
 a sensing region capable of having the small particles thereat with at least a portion of the small particles being optically absorbing particles;
 a high intensity laser light source having a cavity with said sensing region within said cavity and with said high intensity laser light source providing laser light at said sensing region within said cavity for contact with the small particles thereat to cause resulting light that includes light emitted due to incandescence of said optically absorbing particles at said sensing region and also includes light elastically scattered by the small particles at said sensing region; and
 a plurality of optical detecting units each receiving said resulting light with at least a first one of said optical detecting units detecting resulting light that includes said light emitted due to incandescence of said optically absorbing particles and providing an output indicative of said light emitted due to incandescence of said optically absorbing particles, and with at least a second one of said plurality of optical detecting units detecting said resulting light due to said light elastically scattered by the small particles and providing an output indicative of said light elastically scattered by the small particles, the outputs of said plurality of optical detecting units enabling predetermined particles characteristic determination of the small particles.

58. A device for small particle characteristic determination, said device comprising:
 a sensing region capable of having the small particles thereat with at least a portion of the small particles being optically absorbing particles;
 a high intensity laser light source that includes a laser cavity with laser light therein and with said sensing region being within said laser cavity, said laser light at said sensing region being elastically scattered by the small particles and said laser light at said sensing region heating said optically absorbing particles to a temperature at which a detectable level of incandescent light is emitted;
 a first optical detecting unit receiving light from said sensing region, said first optical detecting unit including a first detector that provides an output indicative of said elastically scattered light within a first wavelength range;
 a second optical detecting unit receiving light from said sensing region, said second optical detecting unit including a second detector that provides an output indicative of said emitted light within a second wavelength range;
 a third optical detecting unit receiving light from said sensing region, said third optical detecting unit including a third detector that provides an output indicative of said emitted light within a third wavelength range; and
 a processing unit for receiving said outputs from said first, second, and third optical detecting units and, responsive thereto, providing an output indicative of particle characteristics of the small particles, including particle size and composition of said optically absorbing particles.

* * * * *